(12) United States Patent
Bavari et al.

(10) Patent No.: US 8,936,915 B2
(45) Date of Patent: Jan. 20, 2015

(54) CLEAVAGE SENSITIVE ANTIBODIES AND METHODS OF USE THEREOF

(75) Inventors: Sina Bavari, Frederick, MD (US); Jonathan E. Nuss, New Market, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 13/387,124

(22) PCT Filed: Aug. 17, 2010

(86) PCT No.: PCT/US2010/045811
§ 371 (c)(1),
(2), (4) Date: Jan. 26, 2012

(87) PCT Pub. No.: WO2011/022438
PCT Pub. Date: Feb. 24, 2011

(65) Prior Publication Data
US 2012/0122127 A1    May 17, 2012

Related U.S. Application Data

(60) Provisional application No. 61/234,813, filed on Aug. 18, 2009.

(51) Int. Cl.
*G01N 33/53* (2006.01)
*C07K 16/28* (2006.01)
*C12Q 1/37* (2006.01)
*G01N 33/68* (2006.01)

(52) U.S. Cl.
CPC . *C07K 16/28* (2013.01); *C12Q 1/37* (2013.01); *G01N 33/6854* (2013.01); *G01N 2333/33* (2013.01); *C07K 2317/34* (2013.01)
USPC .............................. 435/7.1; 435/7.2

(58) Field of Classification Search
None
See application file for complete search history.

(56) References Cited

U.S. PATENT DOCUMENTS

| 5,962,637 A | 10/1999 | Shone et al. |
| 5,965,699 A | 10/1999 | Schmidt et al. |
| 8,198,034 B2 * | 6/2012 | Fernandez-Salas et al. ... 435/7.1 |

OTHER PUBLICATIONS

Ferracci, G. et al. Synaptic vesicle chips to assay botulinum neurotoxins. Biochem. J. 2005, vol. 391, pp. 659-666 See abstract and Fig. 2.

Hines, H.B. et al. Use of a recombinant fluorescent substrate with cleavage sites for all botulinum neurotoxins in high-throughput screening of natural product extractions for inhibitors of serotypes A, B and E. See Fig 1 and p. 654, right column.

Hines, H.B. et al. Use of a recombinant fluorescent substrate with cleavage sites for all botulinum neurotoxins in high-throughput screening of natural product extractions for inhibitors of serotypes A, B and E. See Fig 1 and p. 654, right column, 2008 publication year.

* cited by examiner

*Primary Examiner* — Jacob Cheu
(74) *Attorney, Agent, or Firm* — Elizabeth Arwine

(57) ABSTRACT

We disclose cleavage-sensitive antibodies with epitopes spanning the scissile bond of the toxins molecular target protein, enabling toxin-associated proteolysis to be measured in a variety of assay formats.

14 Claims, 15 Drawing Sheets

SNAP-25

Figure 3:
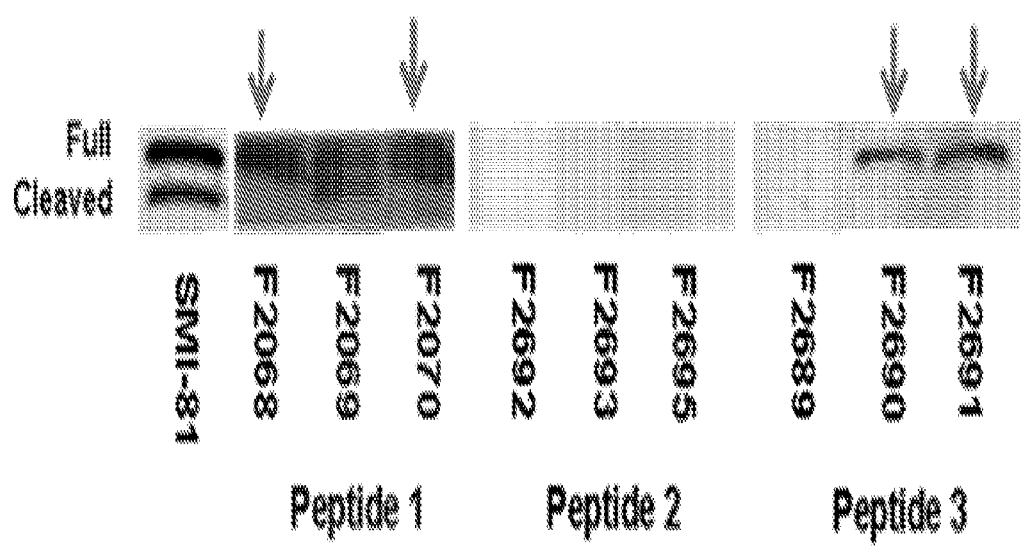

MAEDADMRNELEEMQRRADQLADESLESTRR
MLQLVEESKDAGIRTLVMLDEQGEQLDRVEEG
MNHINQDMKEAEKNLKDLGKCCGLFICPCNKL
KSSDAYKKAWGNNQDGVVASQPARVVDERE
QMAISGGFIRRVTNDARENEMDENLEQVSGII
GNLRHMALDMGNEIDTQNRQIDRIMEKADSN
K-RIDEAN QRATKMLGSG

BoNT/A cleavage sensitive antibody

Labeled secondary antibody

Generation of Immunoreactive signal

→ BoNT/A →

SNAP-25

MAEDADMRNELEEMQRRADQLADESLESTRR
MLQLVEESKDAGIRTLVMLDEQGEQLDRVEEG
MNHINQDMKEAEKNLKDLGKCCGLFICPCNKL
KSSDAYKKAWGNNQDGVVASQPARVVDERE
QMAISGGFIRRVTNDARENEMDENLEQVSGII
GNLRHMALDMGNSDTQNRQIDRIMEKADSN
K-RIDEAN

+

QRATKMLGSG

Loss of immunoreactive signal

FIG. 1

SNAP-25 maeadnmeleenqradqadesestmmlqveeekdagirt
lvmldeggeqtdrveegmnhnqdmkeaekniikdgiccgiicpc
nkikssday-kawgnnqtgvasqparwvdereqmaisggfmvt
ndarenemderieqvsqlnrhmaldngreidtqnqidimeka
dsnktrideanq ratkmlgsg rideanq ratkmlgsg BoNT A Cleavage site Peptide 1 rideanq ratkmlgsg
Peptide 2 deanq ratkmlgsg
Peptide 3 rideanq ratkmlg

CLEAVAGE SENSITIVE ANTIBODIES AND METHODS OF USE THEREOF

CROSS REFERENCE TO RELATED APPLICATION

This application claims the benefit of U.S. Provisional Application No. 61/234,813, filed Aug. 18, 2009, which is hereby incorporated by reference in its entirety.

RIGHT IN THE INVENTION

This invention was made with support from the United States Government and, specifically, the United States Army Medical Research Institute of Infectious Diseases, and, accordingly, the United States government has certain rights in this invention.

BACKGROUND

1. Technical Field

This invention is directed generally to a method and system of assaying biologically relevant activity and, in particular, the assay of protease activity using cleavage sensitive antibodies.

2. Background

Botulism is a potentially fatal disease caused by botulinum neurotoxins (BoNTs) secreted by anaerobic spore-forming bacteria *Clostridium botulinum* (1, 2). Historically, botulism has been associated with food poisoning. The first account of the disease was recorded in 1735 when an outbreak of botulism in Europe was linked to tainted sausage (botulus is Latin for sausage) (3). Today, sporadic outbreaks of food-borne botulism generally result from contaminations occurring at commercial canneries, with the most recent incident in the United States occurring in 2007 (4). Also, infant botulism leads to the hospitalization of nearly 100 children annually in the U.S. alone (5, 6).

Though BoNTs are the most potent of biological poisons, purified BoNTs have found widespread use in medical clinics, and are used to treat a wide array of ailments including the cosmetic appearance of facial wrinkles, cervical dystonia, migraine headaches, and anal fissure (7-10). However, the growing use of these toxins as therapeutic agents makes unintentional overdosing increasingly likely. In addition to accidental or unintentional environmental exposure, the current political climate makes the malicious misuse of BoNTs, through acts of terrorism, a serious possibility (11). Hence, the health threat posed by BoNTs continues to grow. Yet at this time, only limited therapeutic options are available to treat botulism (12). The most common treatment consists of long-term supportive care involving mechanical respiration. Additionally, treatment with BABYBIG™ (anti-BoNT immunoglobulins derived from human serum, California Department of Health Services, Berkley, Calif.) decreases the length of hospitalization in cases of infant botulism, adding credence to the potential benefits of anti-toxin intervention against this disease (13). Currently, BABYBIG and bivalent (BoNTs A/B) equine antitoxin (approved for use in adults) are the only FDA-approved treatments available. Clearly, there is a need to develop novel therapeutics to aid in the recovery from botulism.

Pathophysiology

There are seven biochemically distinct BoNT serotypes (designated A-G). BoNT holotoxins are composed of two subunits: a heavy chain (HC) and light chain (LC), which are connected by a disulfide bridge (2, 14). For all BoNT serotypes, the mechanism of toxicity involves two basic steps: toxin entry into neurons followed by soluble N-ethylmaleimide-sensitive factor attachment protein receptor (SNARE) protein cleavage (15). The toxin entry step is mediated by the HC, as domains located within this subunit interact with neuronal surface receptors that trigger endocytosis (2, 14). Within the endosome, the toxin dissociates into subunits, where the HC may serve an additional function by acting as a chaperone that assists refolding of the LC into its catalytically active conformation(s) (16). Once activated, neuronal function is disrupted by the proteolytic activity of the LC. Specifically, the LC (also referred to as the catalytic domain) is a zinc (Zn) metalloprotease that cleaves SNARE proteins, which mediate the exocytosis of neurotransmitter contained within synaptic vesicles (2). Different BoNT serotypes cleave different SNARE protein components, and/or different sites within the same component. For BoNT serotype A (BoNT/A), the cleavage of SNARE component SNAP-25 (synaptosomal-associated protein of 25 kDa) between glutamine 197 and arginine 198 results in the inhibition of acetylcholine release into neuromuscular synapses, and the flaccid paralysis ensues (17, 18).

High-Throughput Assay

In order to rapidly identify and characterize BoNT inhibitors in cellular models, high-throughput assays must be established. Primary chick neurons are a sensitive cellular model system for studying BoNT intoxication, and successfully measure toxin activity in neurons by quantitating the cleavage of the BoNT/A substrate, SNAP-25, using commercially available antibodies in conjunction with immunoblotting (19). While this analytical method has been reliable, the assay is not amenable to high-throughput screening. To eliminate this research bottle neck the present invention discloses BoNT/A cleavage sensitive (BACS) antibodies which are capable of measuring the BoNT/A catalyzed proteolysis of SNAP-25 in a variety of assay formats. All assays can be conducted in multi-well plates and are amenable for high-throughput analysis. Thus when coupled with cellular models these assays can be used for a broad range of applications such as drug development (the evaluation of toxin antagonists, the evaluation of toxin activators, compound library screening) and BoNT biopharmaceutical manufacturing assays (quality control, product formulation requirements).

Botulinum types A and E toxins cleave protein SNAP-25. Botulinum types B, D, F and G and tetanus toxins cleave vesicle-associated membrane protein (VAMP—also called synaptobrevin). Botulinum type C toxin cleaves the protein syntaxin.

While protease assays are known in the art, they are based on synthetic substrates that are only viable in vitro. The novelty and utility of the present invention is that the disclosed assays can detect the cleavage of proteins such as endogenous SNAP-25 making them effective in vivo as well as in vitro which has far reaching implications for the advancement of the art.

U.S. Pat. No. 5,965,699 to Schmidt et al. discloses a label-based assay for the determination of type A botulinum toxin enzymatic (proteolytic) activity. However, the assay relies on labeling SNAP-25 residues with fluorescamine in vitro and is specifically designed to avoid using animals and cell cultures.

U.S. Pat. No. 5,962,637 to Shone et al, uses synthetic peptide substrates in a fluorescence resonance energy transfer (FRET) based solid-phase microtitre based in vitro assay using antibodies that recognize only post-proteolytic cleavage sites.

The assays of Schmidt et al. and Shone et al. only work in vitro so they only measure the proteolytic activity of BoNTs.

The various embodiments of the assay of this invention work in living systems and, therefore, can be used to measure additional steps of intoxication; most notably toxin entry into cells. For example, small molecules that prevented toxin entry into cells would register as a potential lead compound in a BACS antibody/cellular based compound screen but not in a screen that only measured proteolytic activity in vitro.

The assays of Schmidt et al. and Shone et al. could be used for compound screening and evaluation in vitro (biochemical assay system). The various assays disclosed as embodiments of this invention could also be used to evaluate and screen compounds in vitro but more importantly compounds could be evaluated in cellular models of intoxication which are more stringent models for drug development. BACS antibody/cellular evaluation would allow important issues such as compound toxicity, bioavailability and intracellular efficacy to be assessed during primary screens. These parameters are not measurable in cell free systems.

The assays of Schmidt et al. and Shone et al. could be used to measure the activity of batches of BoNTs in vitro for quality control purposes. However, these assays only measure the proteolytic activity of the light chain. The BACS antibody/cellular assays of the various embodiments of the present invention would provide a more stringent evaluation of BoNT samples (which are often produced in bulk for medical applications) as they allow additional properties of the toxin to be assessed. Toxin entry into cells is mediated entirely by the toxin's heavy chain. A cellular assay of the toxin's activity (such as disclosed in the present application) allows the heavy chain mediated entry activity to also be evaluated in addition to the proteolytic activity mediated by the toxin's light chain. In vitro assays such as those designed by Schmidt et al. and Shone et al. only measure a single property (the proteolytic activity) of the toxin, thus batches of toxin with defective heavy chains but functional light chains would register as acceptable by in vitro assays but not by more stringent BACS/cell based assays.

The BACS antibody based assays could also be used in other living systems to study the effects of BoNTs in vivo, such as, by way of nonlimiting example, measurement of SNAP-25 cleavage in laboratory animals or patients from biopsy (by immunofluorescence microscopy). These studies will help understand the pharmokinetics of the toxin in whole animal systems and allow the neuron function of patients suffering from botulism to be evaluated. Neither of these applications are possible using currently available technology.

SUMMARY

Botulinum neurotoxins (BoNTs) are zinc-metalloproteases that cleave components of the SNARE (soluble N-ethylmaleimide-sensitive factor attachment protein receptor) protein complex, inhibiting acetylcholine release into neuromuscular junctions, resulting in flaccid paralysis and eventual death. The potential for the malicious misuse of these toxins as bioweapons has created an urgent need to develop effective therapeutic countermeasures. Robust cell-based assays will be essential for lead identification and the optimization of therapeutic candidates. The various embodiments of the present invention include novel BoNT serotype A (BoNT/A) cleavage-sensitive (BACS) antibodies that only interact with full-length SNAP-25 (synaptosomal-associated protein of 25 kDa), the molecular target of the BoNT/A serotype (FIG. 1). These antibodies exhibit high specificity for full-length SNAP-25, allowing the BoNT/A-mediated proteolysis of this protein to be measured in diverse assay formats, including several variations of ELISA (enzyme-linked immunosorbent assay) and multiple immunofluorescence methods. Assays built around the BACS antibodies have excellent sensitivity, excellent reproducibility, and are amenable to multi-well formats. Furthermore, the various embodiments of the invention also include novel methods for evaluating BoNT/A activity in cellular models of intoxication and high-throughput evaluation of experimental compounds.

One embodiment of the invention relates to an assay for botulinum toxin or tetanus toxin comprising the steps of:

(a) combining a test compound with a substrate and with antibody, wherein the substrate has a cleavage site for the toxin and when cleaved by toxin forms a product, and wherein the antibody binds to the substrate but not to the product; and (b) testing for the presence of antibody bound to the substrate.

Preferably, in the practice of this invention, the substrate is a peptide or a protein which is cleaved by the toxin to generate new peptides products. The assay according to the invention may utilize an antibody that binds to the substrate peptide but not to the cleavage products and may comprise the steps of: (a) combining a test compound with the substrate peptide to form an assay mixture, wherein the substrate peptide is selected from intact peptides or fragments thereof selected from the group consisting of VAMP; a VAMP analog; a VAMP isoform; SNAP-25; a SNAP-25 analog; a SNAP-25 isoform; syntaxin; a syntaxin analog; and a syntaxin isoform; or a fragment thereof; (b) combining the assay mixture with the antibody, and (c) determining whether there has been formed any conjugate between the antibody and the substrate.

In one embodiment, the assay further comprises of an antibody adapted selectively to bind to a peptide selected from a group consisting of SEQ ID NOS: 1, 2 and 3.

The present invention also relates to a method of obtaining an antibody adapted selectively to bind to the scissile bond of a toxin's molecular target, enabling toxin-associated proteolysis to be measured in a variety of assay formats, the method comprising identifying at least one antigentic peptide that correspondent to the toxin's cleavage site in the molecular target, immunizing an animal against at least one said antigentic peptide, isolating antibodies that bind to said antigentic peptide(s) and recovering said antibody.

In one embodiment, the method of obtaining an antibody adapted selectively to bind to the scissile bond of a toxin's molecular target preferably comprises immunizing an animal with an antigen selected from a group consisting of: SEQ ID NOs 1, 2 and 3 and a carrier molecule, and isolating the antibody that binds to said antigen. Acceptable carrier molecules are well known in the art and include, by way of non-limiting example: Keyhole Limpet Hemocyanin, Bovine Serum Albumin and Ovalbumin.

The invention also relates to a toxin assay kit comprising: (1) an assay component according to the invention; (2) an antibody according to the invention which is identified immunohistochemically; and (3) an assay substrate.

Other embodiments and advantages of the invention are set forth in part in the description, which follows, and in part, may be obvious from this description, or may be learned from the practice of the invention.

DESCRIPTIONS OF THE DRAWINGS

FIG. 1. A diagram representing the mode of action of the BoNT/A cleavage sensitive antibodies (BACS). BACS antibodies bind across the BoNT/A cleavage site on SNAP-25. This binding event can be used to generate a measurable signal which correlates with the concentration of the full length protein substrate. BoNT/A cleavage destroys the BACS antibody epitope resulting in loss of immunoreactivity and loss of signal.

FIG. 2. A diagram showing the three designed peptides used for vaccination span the BoNT/A cleavage site in SNAP-25. Sequences shared between peptides are shown in light-gray highlights, while N-terminal and C-terminal additions are shown as underlined and dark-gray, respectively.

FIG. 3. Photographs of Western blot analysis of N-terminal antibody (SMI-81) and BACS antibodies. Four of the antibodies (indicated by arrows on the figure) only bind full length SNAP-25 by comparison the N-terminal specific antibody also interacts with the proteolysed form of SNAP-25.

Figure 4:
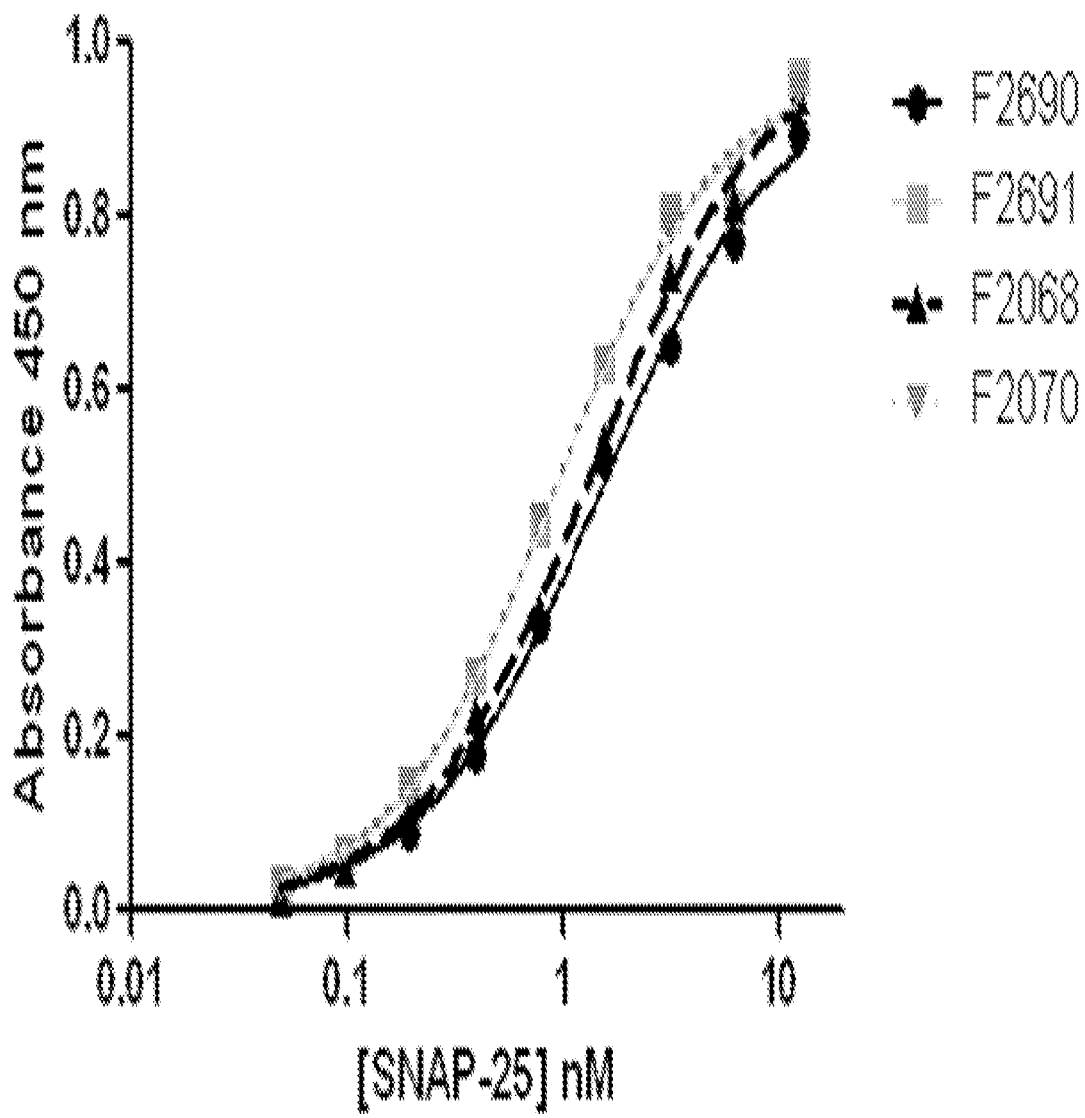

FIG. 4. Characterization of the binding affinity of BACS antibodies. Multi-well plates were coated with a dilution series of SNAP-25 and binding affinities were measured by ELISA. All four antibodies displayed sigmoidal binding characteristics and possess dissociation constants that range from 0.92 to 1.48 Nm.

Figure 5:
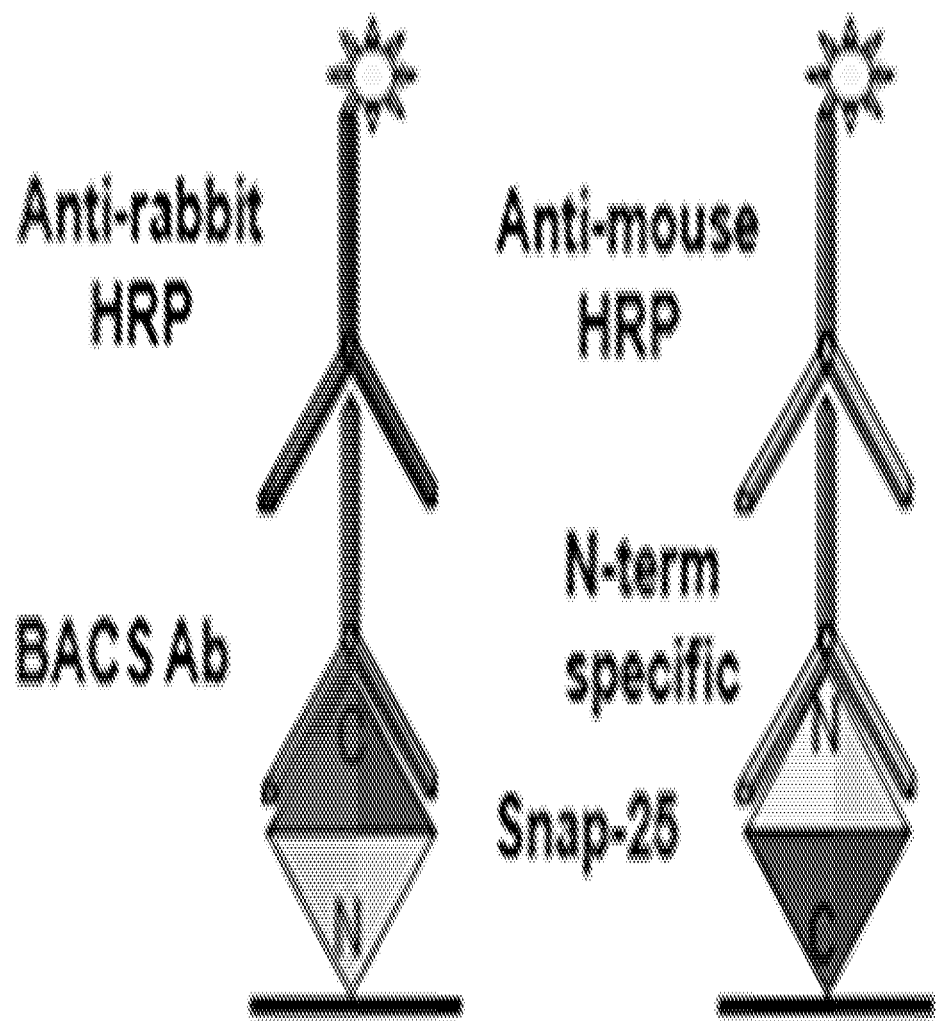

FIG. 5. A drawing of a direct ELISA process using BACS antibody F2691 and commercially available cleavage insensitive antibody (66066).

Figure 6:
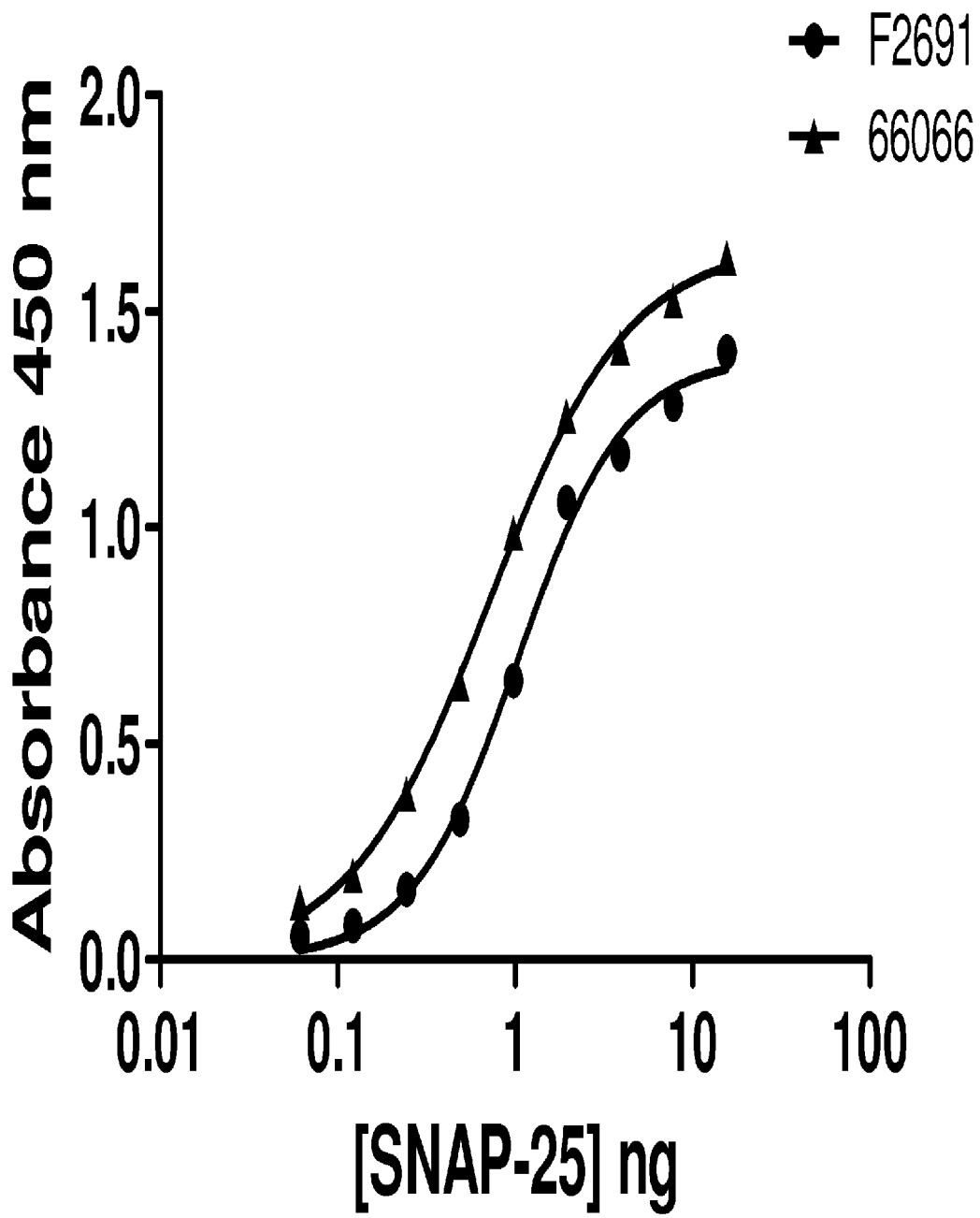

FIG. 6. A graph showing that both antibodies (F2691 and 66066) interact with recombinant SNAP-25.

Figure 7:
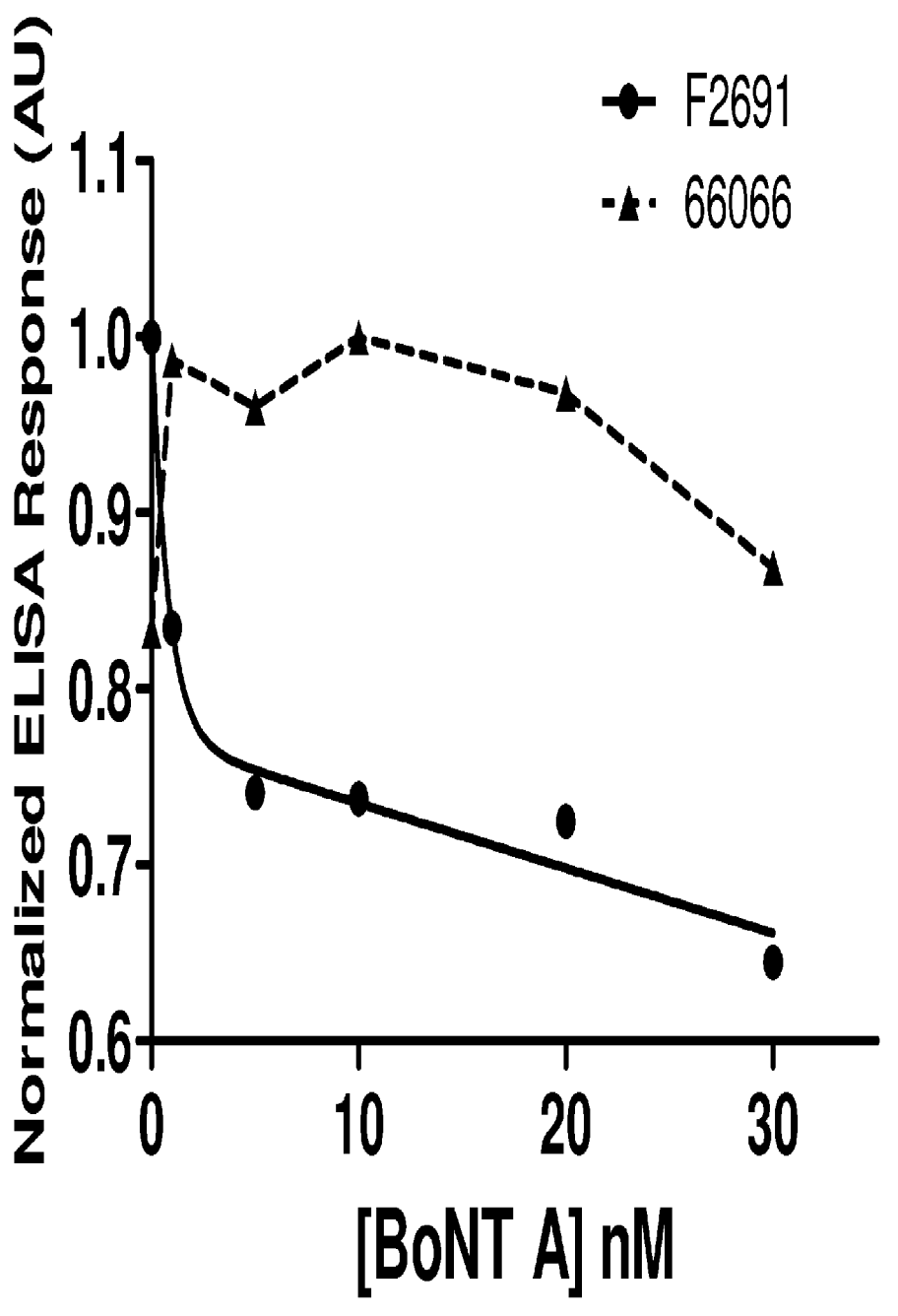

FIG. 7. A graph showing ELISA response for both F2691 and 66066 antibodies in neuron lysate treated with 0-30 Nm BoNT/A. The signal generated with BACS antibody F2691 shows dose response commensurate with BoNT/A concentration.

Figure 8:
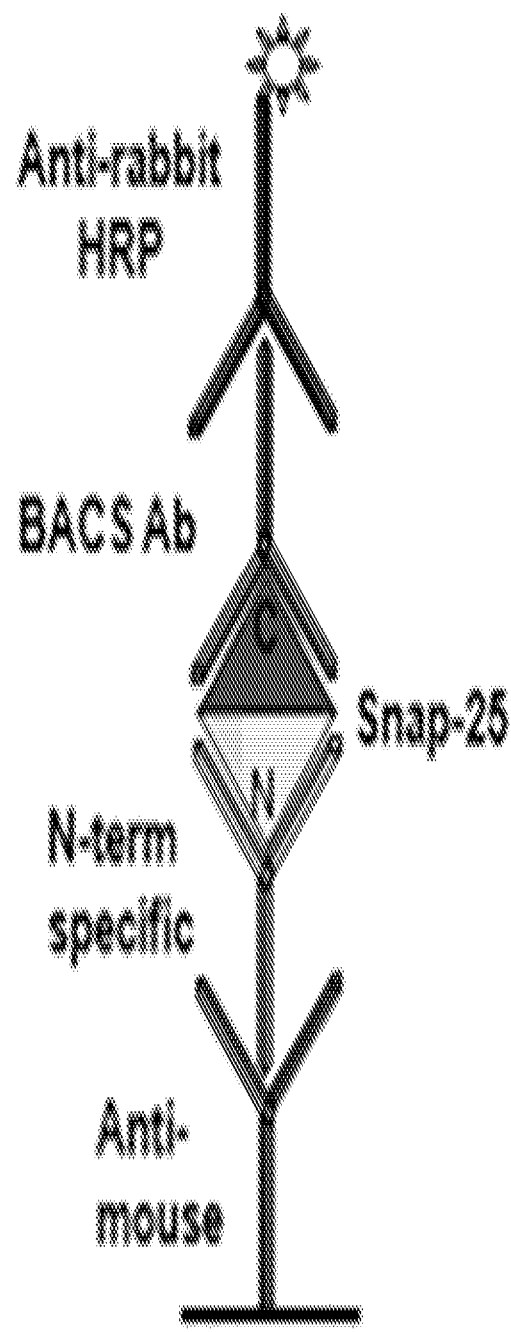

FIG. 8. A drawing of a capture ELISA process using the N-terminal antibody 66066 and the cleavage sensitive antibody F2070.

Figure 9:
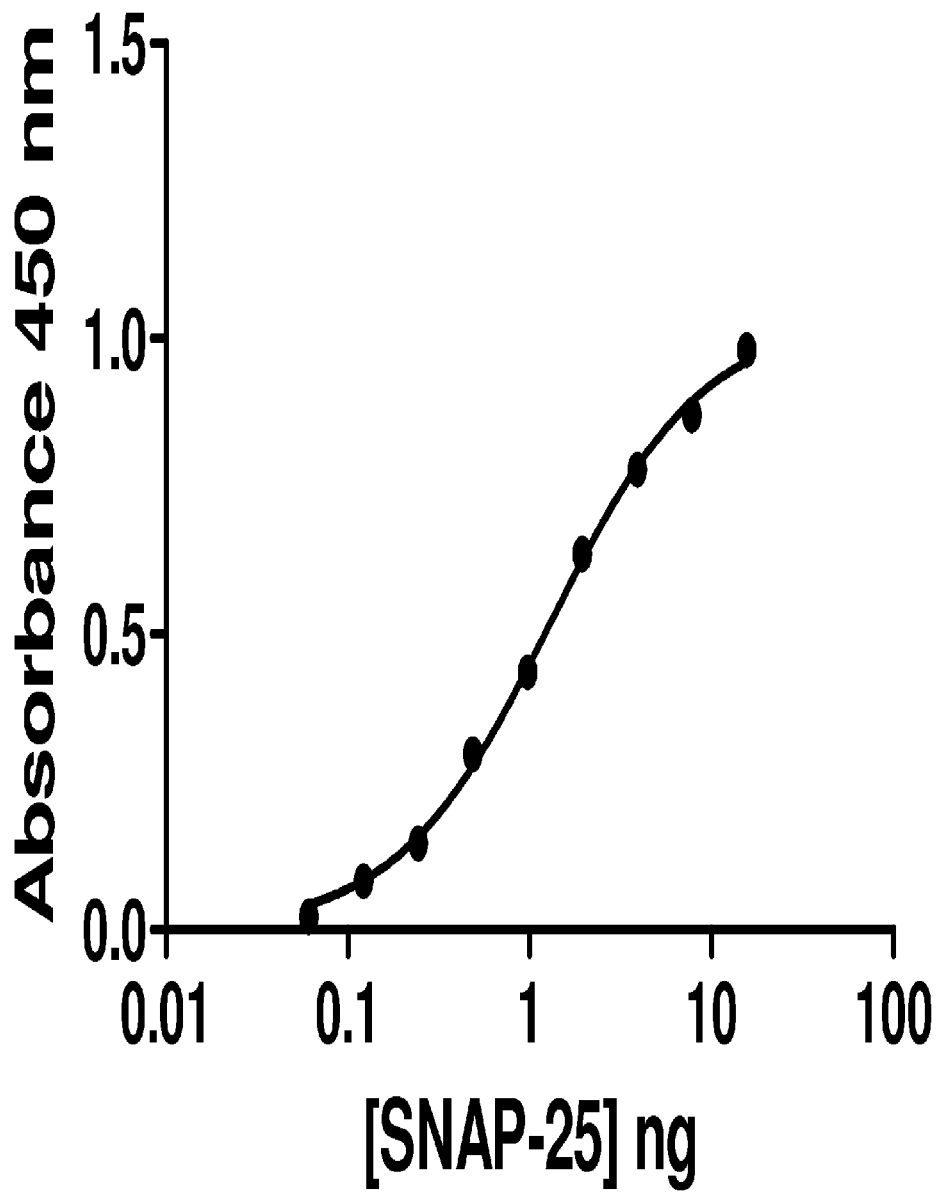

FIG. 9. A graph demonstrating that the combination of 66066 and F2070 antibodies avidly binds and detects recombinant SNAP-25.

Figure 10:
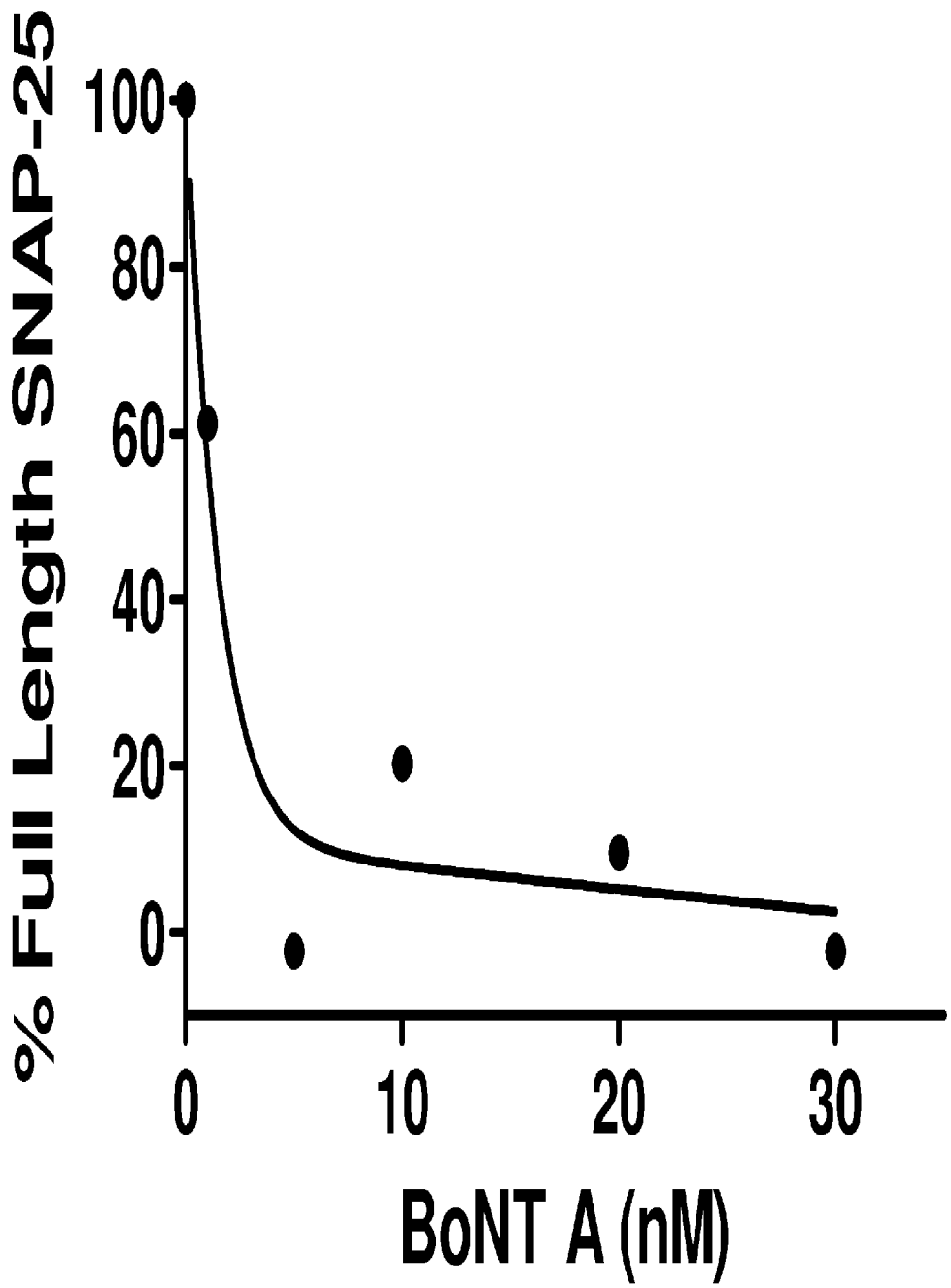

FIG. 10. A graph showing the amount of captured full length SNAP-25 from neuron lysate treated with 0-30 Nm BoNT/A.

Figure 11:
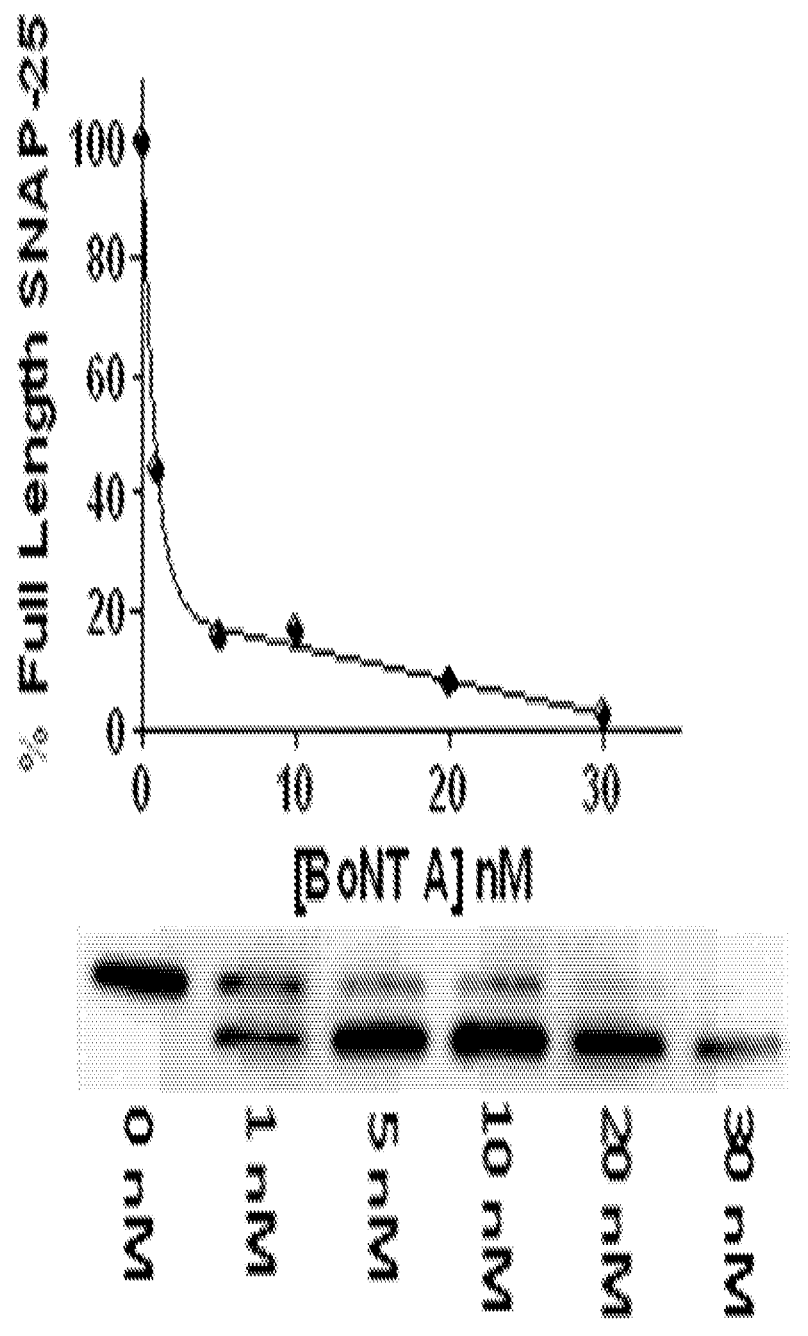

FIG. 11. A graph and photograph showing the amount of full length SNAP-25 measured by Western blot analysis as a function of BoNT/A concentration. ELISA signals measured using BACS antibodies (FIGS. 7 & 10) show similar dose-dependent responses.

Figure 12:
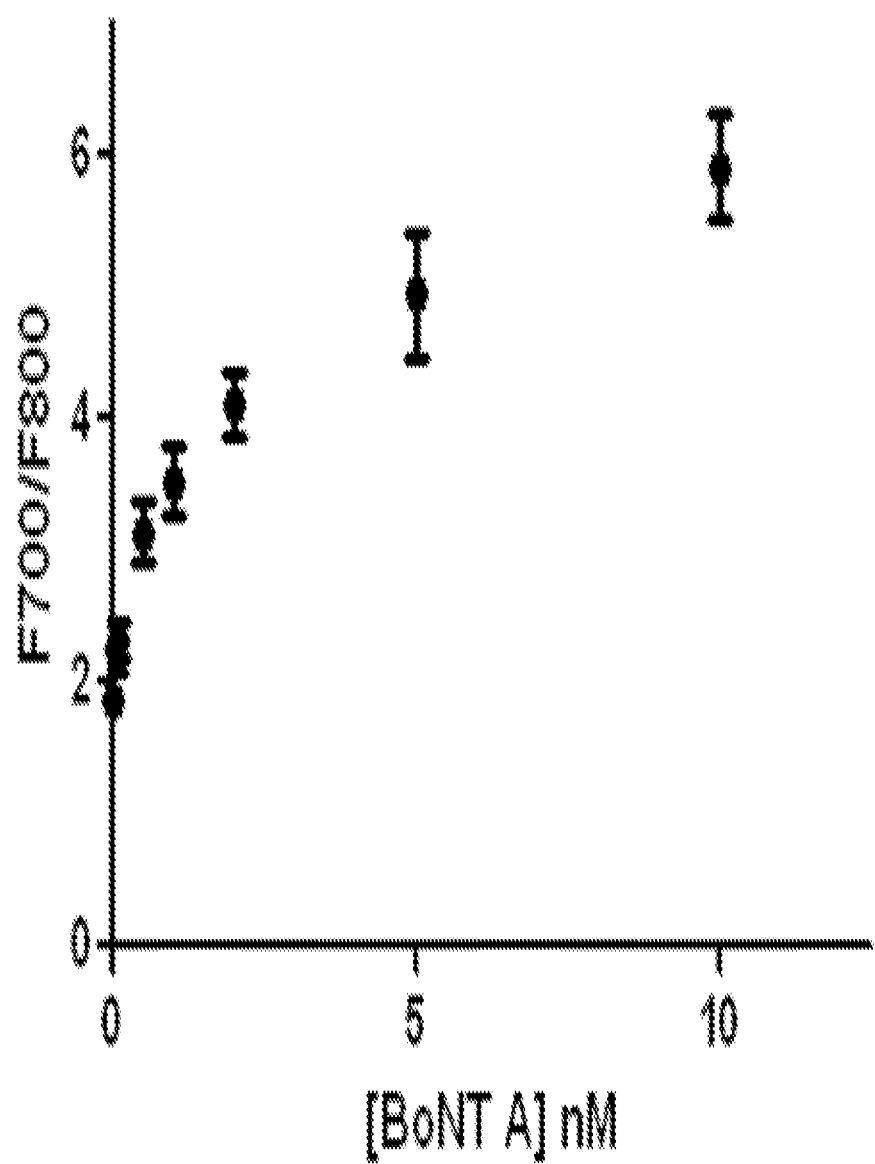

FIG. 12. A graph of average fluorescence ratios (intensities at 700/800 nm which corresponds to total SNAP-25/full length SNAP-25) measured by low resolution fluorescence imaging using BACS antibodies plotted against BoNT A toxin concentration. Data presented in the graph are average values of six replicates, and error bars represent standard errors of the averages.

Figure 13:
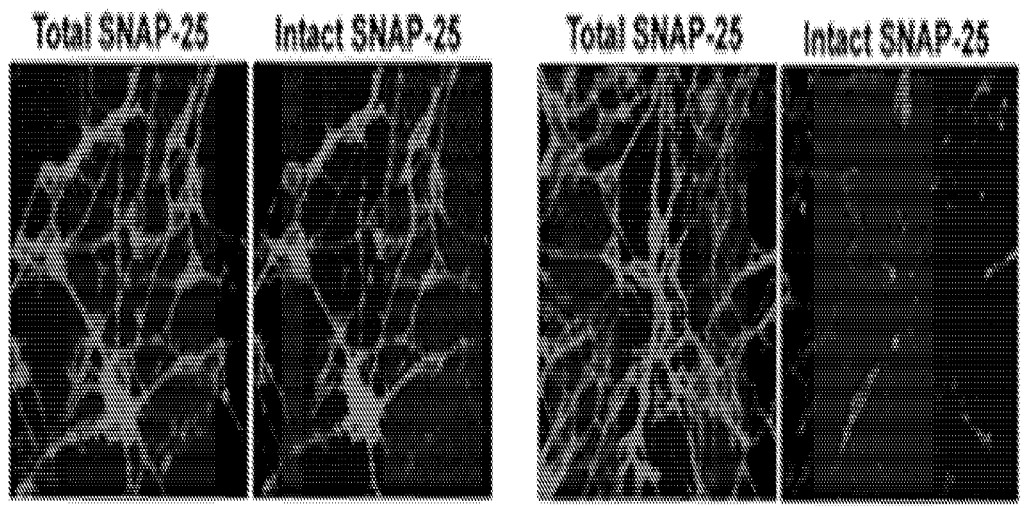

FIG. 13. A panel of photographs showing high resolution immunofluorescence analysis using N-terminal antibody SMI-81 and BACS antibody F2070. After a 3 hour exposure to 5 Nm BoNT A, cleaved SNAP-25 is recognized by SMI-81 but not by F2070, resulting in a reduction in fluorescence.

Figure 14:
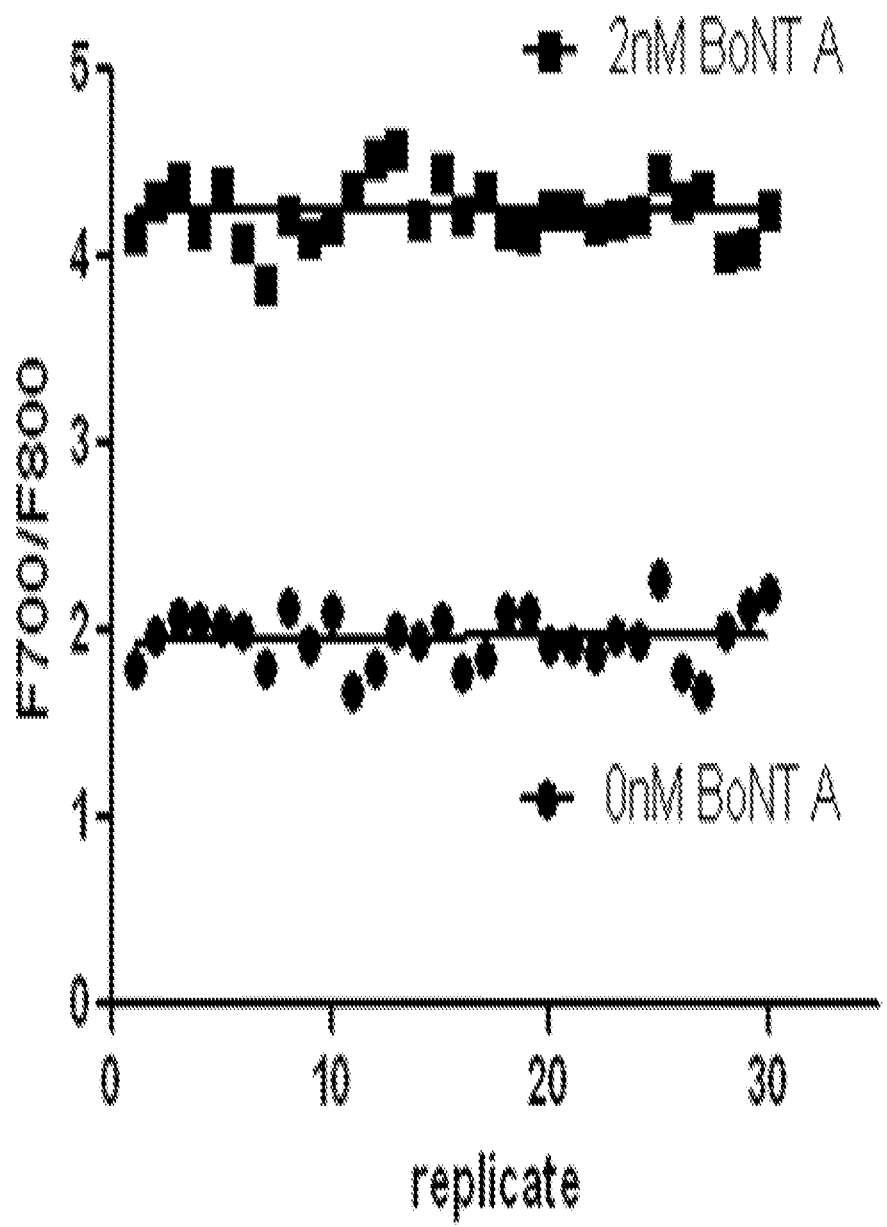

FIG. 14. A graph demonstrating assay stability validation. Chick motor neurons were harvested and transferred to a 96 well plate. Half of the plated cells were intoxicated with 2 Nm BoNT/A and the other half were incubated with media alone. After a 3 hour incubation period, cells were fixed, stained with N-terminal specific antibody SMI-81, BACS antibody F2070, and their cognate fluorescently labeled secondary antibodies, and analyzed using the low resolution intracellular fluorescence assay (in-cell Western blot analysis). Fluorescence intensity in each channel was calculated for each well, and the ratio of intensities at 700 and 800 nm (corresponding to total SNAP-25/Full length SNAP-25) was plotted against well position (i.e., replicate).

Figure 15:
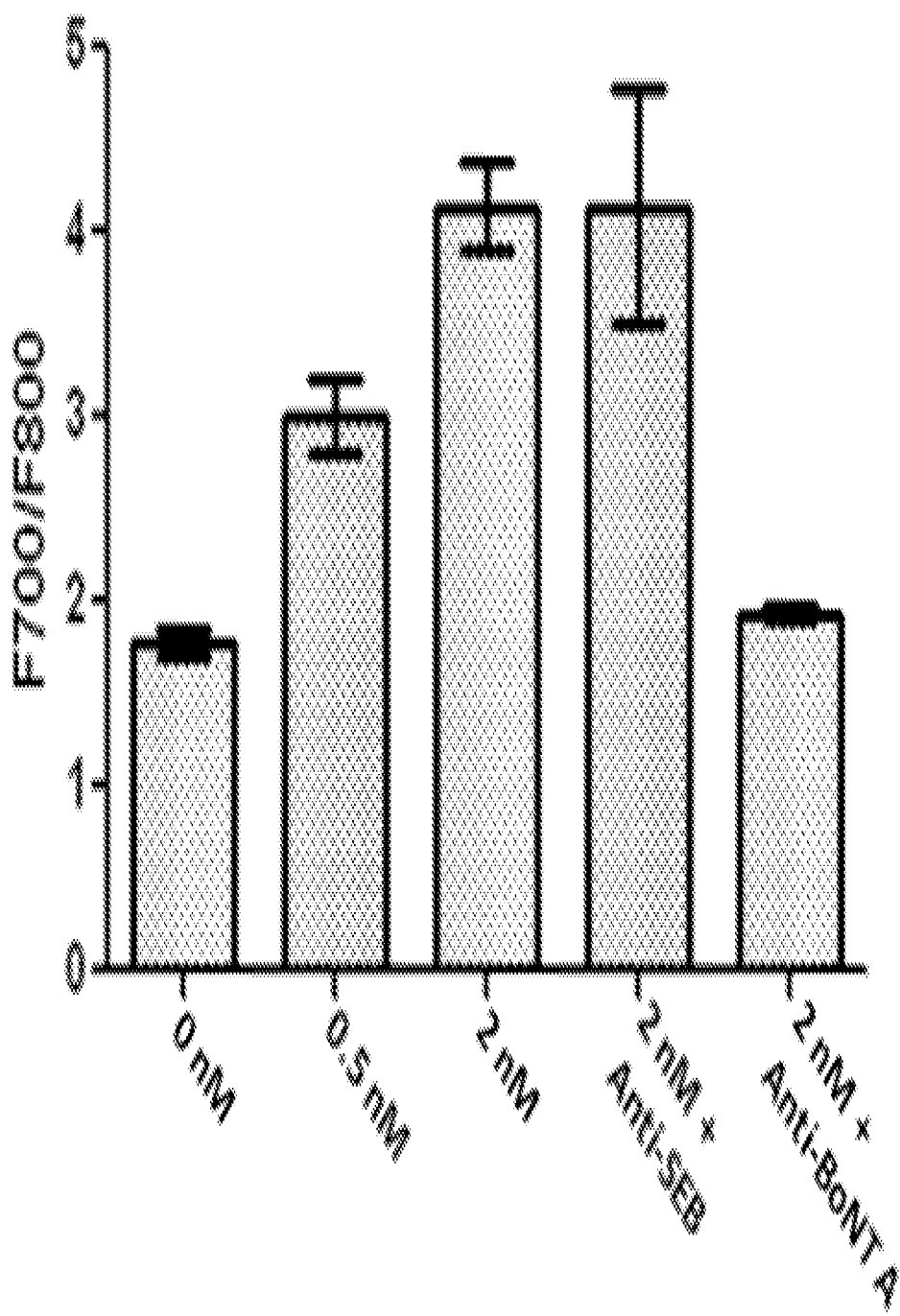

FIG. 15. A graph depicting the results of a BACS assay performance using a known BoNT/A antagonist. Neurons were harvested, plated, incubated with media containing BoNT/A (0, 0.5 or 2 Nm) or BoNT/A (2 Nm) plus antibody, and analyzed by the standardized BACS low resolution fluorescence assay. A staph enterotoxin B (SEB) neutralizing antibody did not affect BoNT/A toxin activity, but a previously characterized neutralizing antibody (4A2-4, i.e., Anti-BoNT/A) efficiently inhibited SNAP-25 cleavage at 2 Nm BoNT/A. Data presented in the bar graph are average values of six replicates, and error bars represent standard errors of the averages.

DETAILED DESCRIPTION OF THE PREFERRED EMBODIMENTS

In the following detailed description, for purposes of explanation, numerous specific details are set forth in order to provide a thorough understanding of the various embodiments of the present invention. It will be apparent, however, that the various embodiments of the present invention may be practiced without these specific details. In other instances, well-known structures and devices are schematically shown in order to simplify the drawing.

Suitable substrates for the toxin assay include the protein families VAMP (also known as synaptobrevin), SNAP-25,35 and syntaxin. Each of these protein families comprises several isoforms and analogues which are detailed below.

In mammals, VAMP (or synaptobrevin) has isoforms 1 and 2, and cellubrevin which is found in non-secretary cells. There may be other isoforms in exocrine cells.

SNAP-25 also has two known isoforms (a and b) and an analogue called SNAP-23.

Syntaxin has large number of isoforms, divided into groups 1-6. Some of these isoforms have sub-groups.

Detailed descriptions of the various members of the substrate protein families are given in the following published papers, which are hereby incorporate by reference in their entirety:

VAMP:
Archer, III, B. T, Ozcelik, T, Jahn, R., Francke, U. and Sudhof, T. C., "Structures and chromosomal localizations of two human gene encoding synaptobrevins 1 and 2,". Biol. Chem. 265: 17267-17273 (1990).

SNAP-25:
Oyler, G. A., Higgins, G. A., Hart, R A., Battenberg, E., Billingsley, M., Bloom, F. E. and Wilson, M. C., "The identification of novel synaptosomal-associated protein SNAP-25, differentially expressed in neuronal subpopulations," J. Cell Biology 109: 3039-3052 (1989).

Schiavo, G., Santucci, A., DasGupta, B. R, Mehta, P. P., Jontes, J., Benfenati, F., Wilson, M. C., and Montecucco, C., "Botulinum neurotoxins serotypes A and E cleave SNAP-25 at distinct COOH-terminal peptide bonds," FEES Lett. 335: 50 99-103 (1993).

Syntaxin:
Bennett, M. K., Calakos, N., and Scheller, R. H., "Syntaxin: a synaptic protein implicated in docking of synaptic vesicles at presynaptic active zones," Science 257: 255-259 55 (1992).

The substrate for the assay is therefore selected from the group consisting of VAMP; VAMP analogs; VAMP isoforms; SNAP-25; SNAP-25 analogs; SNAP-25 isoforms; syntaxin; syntaxin analogs and syntaxin isoforms. References hereafter to VAMP, SNAP-25 and syntaxin are to be understood as references to all member of each family of proteins.

In one embodied method of the invention, an antibody can be linked to an enzyme and the antibody on the plate can be measured by adding a substrate and observing conversion into a detectable product. Suitable reporter enzymes that may be used are well known in the art and include, but are limited to, malate dehydrogenase, staphylococcal nuclease, delta-V-steroid isomerase, yeast alcohol dehydrogenase, alpha-glycerophosphate dehydrogenase, triose phosphate isomerase, alkaline phosphatase, asparaginase, glucose oxidase, betagalactosidase, ribonuclease, urease, catalase, glucose-VIphosphate dehydrogenase, glucoamylase and acetylcholine esterase.

Radioisotopes that may be linked to the antibody of the invention include $^{3}H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$ and $^{75}Se$. Alternatively, the antibody may be linked to a fluorescent compound such as fluorescein isothiocyanate, rhodamine, phycoerythrin, phycocyanin, allophycocyan, o-phthaldehyde and fluorescamine. Chemiluminescent compounds that can be linked to the antibody include luminol, isoluminol, theromatic acridinium ester, imidazole, acridinium salt and oxalate ester. Bioluminescent compounds that may be linked to the antibody include luciferin, luciferase, aequorin and green fluorescent protein.

The antibodies of the invention may be detected by indirect immunohitochemical means such as secondary antibodies.

The assay and assay method may compromise a solid-phase. A suitable solid-phase may be an ELISA plate, bead, dip-stick or any other matrix that can be used for immobilizing the endopeptidase substrate component. The solid-phase component may also be a nitrocellulose membrane or the equivalent as used in the Western blotting technique. Alternatively, the solid phase may be conducted of diazocellulose, glass, polystyrene, polyvinylchloride, polypropylene, polyethylene, dextran, nylon, starch or affinity support gels such as Sepharose and agar.

The solid-phase peptides of the assay are stable and suitable for incorporation into test kits that provide for convenient and efficient toxin assays. Such test kits comprise a carrier means such as a box having therein one or more container means such as vials, tubes, bottles, jars and the like, each of which contain one or more elements that are used in the assays of the invention. For example, a first container means may contain antibodies which have specific binding affinity for the scissile bond of a toxin's target substrate. A second container means may contain one or more substrates that are cleaved by the toxin. Additional container means may contain standard concentrations of toxin that can be used to prepare a standard curve for quantitation of toxin in a test sample.

In other embodiments of the invention the assay is done in vivo for example, through BACS antibody/cellular evaluation.

Generation of BoNT/A Cleavage Sensitive (BACS) Antibodies

BoNT/A cleavage sensitive antibodies (BACS) were generated by vaccinating rabbits with peptides corresponding to the BoNT/A cleavage site in SNAP-25 (FIG. 2). The rationale for the design was based on the fact that BoNT/A cleavage should destroy the epitope, and therefore only the full-length protein should interact with these antibodies. To assure that an acceptable antibody would be produced, three different peptides corresponding to different sequences of the protein were used as immunogens (FIG. 2). After boosting and blood collection, post-vaccine sera from each rabbit were pooled and characterized for binding specificity.

Western Blot Characterization of BACS Antibody Specificity

To characterize the specificity of the generated antibodies, Western blot analysis was used. Primary chick neurons were cultured and treated with BoNT/A (10 Nm) for 5 hr; cells were then harvested and lysed. Whole cell extracts were resolved by SDS PAGE, transferred to PVDF membranes, and probed with post-vaccine sera from each of the vaccinated rabbits or with the control N-terminal specific SNAP-25 antibody, SMI-81 (FIG. 2). Control SMI-81 detected the N-terminal cleavage product as well as full-length SNAP-25. In contrast, four out of nine rabbits (F2068, F2070, F2690 and F2691) produced antibodies that only recognizes full-length SNAP-25 (FIG. 3). Finally, a similar series of Western blot experiments was performed using sera from the four rabbits that generated BACS antibodies. These experiments were performed with either an excess of peptide added during primary antibody incubation, or utilizing pre-vaccine sera from each rabbit. In all four cases, either permutation (adding exogenous peptide or pre-vaccine sera) abrogated immunoreactivity (data not shown). Taken together, these data conclusively demonstrate that these antibodies only interacted with full-length SNAP-25 and this interaction was sensitive to BoNT/A-mediated proteolysis. After verification of binding specificity, affinity chromatography was used to purify each of the four BACS antibodies from pooled sera.

Characterization of Antibody Binding Affinity by ELISA

To measure BACS antibody binding, a dilution series of recombinant SNAP-25 was arrayed in a 96-well plate and analyzed by ELISA using BACS antibodies in conjunction with HRP-labeled secondary antibodies (FIG. 4). All antibodies analyzed displayed sigmoidal binding characteristics and fit well to a one-site binding model, allowing dissociation constants (KDs) to be accurately measured. All KDs displayed low Nm affinities: 0.92+/−0.04, 0.92+/−0.12, 1.38+/−0.13, and 1.48+/−0.14 for BACS antibodies F2070, F2691, F2068, and F2690, respectively.

Direct ELISA Formatted Assay for Measurement of BoNT/A Activity

To allow the sensitive and rapid measurement of BoNT/A activity in a cell-based assay, direct and capture ELISA procedures were established (FIGS. 5 and 8). In the direct ELISA assay, protein was allowed to bind and coat 96-well polystyrene plates, and then a primary antibody (either BACS antibody F2691 or N-terminal specific antibody 66066), in conjunction with secondary antibodies, detected SNAP-25 (FIG. 5). Although all four BACS antibodies interacted avidly with recombinant SNAP-25 (FIG. 4), F2691 was the only antibody with the ability to detect the protein in crude, whole cell samples. For comparative purposes, a commercially available N-terminal antibody 66066 was also found to bind the recombinant protein, and detected SNAP-25 in crude, whole cell samples as well (FIG. 6). To evaluate the activity of the antibodies in biological samples, primary chick neuronal cells were plated and treated with different concentrations of BoNT/A (0-30 Nm). After a five hour incubation period, the cells were harvested, lysed, and total protein quantitated. Cell lysates from these samples were then analyzed by ELISA (FIG. 7) or Western blot analysis using N-terminal specific antibody SMI-81 (FIG. 11).

ELISA assays utilizing the N-terminal antibody (66066) should be insensitive to SNAP-25 cleavage, as the epitope of this antibody is distant from the BoNT/A scissile bond on SNAP-25. Hence, measurements performed with this reagent should detect total (uncleaved and cleaved) SNAP-25 in a sample. Consistent with this hypothesis, the ELISA signal generated with this antibody did not show a trend with increasing toxin concentration (FIG. 7). To measure the concentration of full-length SNAP-25, the ELISA signal obtained from the cleavage-sensitive antibody (F2691) was normalized to the signal obtained from the cleavage-insensitive antibody (66066); thus accounting for variations in total SNAP-25 concentration between samples. Using this approach, the normalized response clearly indicated a decrease in signal with increasing toxin concentration, mirroring the trend observed via Western blot analysis (FIG. 11).

Capture ELISA Formatted Assay for Measurement of BoNT/A Activity

A capture ELISA assay was established utilizing cleavage-sensitive antibody F2070 and the N-terminal antibody described above (66066) (FIG. 8). In this version of the assay, 96-well plates coated with anti-mouse immunoglobulins were used to attach and orient the capture antibody 66066. The capture antibody bound the N-terminus of the antigen (SNAP-25) and allowed the detection antibody (F2070) to interact with the C-terminal portion of the protein. A HRP-labeled anti-rabbit secondary antibody was used to detect antibody binding (FIG. 8). In this format, all four BACS detection antibodies interacted with recombinant SNAP-25, but F2070 bound with the lowest dissociation constant (data not shown). For this reason, F2070 was used to develop the capture ELISA assay, and this combination of capture and detection antibodies avidly bound recombinant SNAP-25 (FIG. 9). To evaluate the assay's in vivo potential, the BoNT/A-treated samples described above were also analyzed by capture ELISA. Using this assay format, percent full-length SNAP-25 could be accurately measured for each toxin concentration (using a standard curve generated using the recombinant protein to calculate the amount of full-length SNAP-25 present in each sample) and these data correlated almost exactly with the changes measured by immunoblot analysis (FIG. 11). Thus, our series of BACS antibodies was capable of monitoring BoNT/A proteolytic activity in multiple ELISA-formatted assays.

Immunofluorescence Assays to Measure BoNT/A Activity in Motor Neurons

To test the efficacy of BACS antibodies in immunofluorescence assays, chick neurons were plated in 96-well plates and treated with different concentrations of BoNT/A (0-10 Nm) (FIG. 12). After fixation and permeabilization, cells were stained with BACS antibody F2070, N-terminal specific antibody SMI-81, and pertinent species specific fluorescent secondary antibodies. Stained plates were then imaged and analyzed using a Li-Cor Odyssey infrared imaging system. In these experiments, fluorescence emission at 700 nm corresponded to SMI-81 immunoreactivity and fluorescence at 800 nm corresponded to BACS antibody F2070 immunoreactivity. Calculating the ratio of fluorescence intensities in both channels (i.e., the fluorescence at 700 nm compared to the fluorescence at 800 nm) allowed changes in full-length SNAP-25 to be measured in each well as a function of BoNT/A concentration. The measured dose-response showed a concentration dependent increase in the ratio of fluorescence measured at 700 nm to the fluorescence signal measured at 800 nm with increasing toxin concentration (FIG. 12). The utility of BACS antibodies was also tested in high-resolution immunofluorescence imaging experiments. In these experiments chick neurons were intoxicated with 5 Nm BoNT/A; control samples were incubated in medium alone (FIG. 13). Neurons were then stained with DAPI to visualize nuclei, N-terminal specific anti-SNAP-25 antibody SMI-81, BACS antibody F2070, and pertinent fluorescent secondary antibodies. This immunostaining procedure yielded high-resolution images of motor neurons with both antibodies detecting SNAP-25 throughout the axons and soma (FIG. 13). Treating neurons with 5 Nm BoNT/A decreased the concentration of uncleaved or "intact" SNAP-25 as detected by BACS antibody F2070, while immunostaining with the N-terminal specific antibody was insensitive to BoNT/A treatment. The changes in full-length SNAP-25 after BoNT/A intoxication were measured by integrating fluorescence intensities in channels detecting total SNAP-25 (N-terminal specific antibody staining) and full-length SNAP-25 (BACS antibody staining), respectively. The ratio of these integrated intensities decreased from 0.90 to 0.13 after intoxication, demonstrating that high-resolution imaging can be used to measure intracellular BoNT/A activity by detecting SNAP-25 cleavage (FIG. 13).

Standardization and Implementation of a High-Throughput Immunofluorescence Assay with BACS Antibodies Given the success of immunofluorescence experiments using BACS antibodies (FIGS. 12, 13), and the simplicity of using low-resolution imaging as an analytical platform (FIG. 12), we established a standardized high-throughput assay to measure BoNT/A activity using a multi-well format and a Li-Cor infrared imaging system. In these experiments, optimal antibody dilutions and imaging parameters were empirically determined. After multiple iterations, a robust and stable assay was established (FIG. 14). The assay was simple to perform, yielded a stable response across the multi-well plate, and allowed for sufficient discrimination of positive (BoNT/A intoxicated samples (2 Nm)) and negative controls (un-intoxicated samples). The z-score for this particular experiment was 0.602, indicating that the assay was appropriate for compound screening and evaluation. As an additional performance benchmark, a known BoNT/A antagonist was evaluated in the assay (FIG. 15). In this experiment neutralizing antibody 4A2-420 or control anti-SEB antibody was added to cells during intoxication with 2 Nm BoNT/A. Under these conditions, antibody 4A2-4 provided nearly complete protection from BoNT/A, as BACS-associated fluorescence equaled un-intoxicated control samples. However, the anti-SEB antibody was completely ineffective against BoNT/A, as cleavage-associated fluorescence measured for these samples equaled uninhibited (treated with 2 Nm BoNT/A) controls (FIG. 15).

We designed BoNT/A cleavage-sensitive antibodies with epitopes spanning the scissile bond of the toxin's molecular target SNAP-25, enabling toxin-associated proteolysis to be measured in a variety of assay formats. Assays utilizing these reagents allowed BoNT/A activity to be directly monitored by detecting cleavage of the toxin's endogenous substrate, as opposed to relying on a surrogate biomarker or use of an engineered exogenous substrate. Because of this caveat, assays with BACS antibodies can be used in assay systems employing untransformed primary neuronal cells, highly sensitive cell models for BoNT intoxication (19). Though data presented here described a suite of antibodies specifically designed to measure BoNT/A activity, similar design strategies could be used to generate antibodies that are sensitive to cleavage by other highly specific proteases.

ELISAs using BACS antibodies could be used to measure changes in immunosorbance that result from the BoNT/A catalyzed proteolysis of SNAP-25 (FIGS. 7 and 10). As is the case for any ELISA, these assays were relatively straightforward to perform and did not require highly specialized laboratory equipment. Of the two versions of ELISA presented here, the direct assay required the fewest steps, and was capable of detecting immunosorbent changes that correlated well with SNAP-25 proteolysis (FIG. 7). However, background signal, presumably caused by nonspecific interactions between detection antibodies and cellular proteins, prevented measuring the percentage of full-length SNAP-25 in experimental samples, and the assay could only be used to compare relative amounts of full-length SNAP-25. To obviate this interference, the capture ELISA, although requiring an additional antibody conjugation step, eliminated interfering cellular proteins during antigen capture. Thus, the capture ELISA can be used to measure the percentage of full-length SNAP-25 in experimental samples, using recombinant SNAP-25 as a standard (FIG. 10).

In contrast to many other analytical techniques, including ELISA, in-cell immunofluorescence assays do not require preparation of protein lysates before analysis. Because these assays circumvent this tedious step, they are more amenable to high-throughput development. Specifically, fluorescence imaging assays utilizing BACS antibodies can be used for either low-resolution imaging analysis or high-resolution imaging, and both techniques allow the accurate measurement of toxin activity (FIGS. 12, 13). Because of the technical simplicity and stability of the low-resolution fluorescence assay, it was further standardized for subsequent use in inhibitor evaluation (FIGS. 14, 15). The assay showed the hallmarks of robustness as it had a z-score greater than 0.6 and clearly identified a known BoNT/A antagonist. The detection of BoNT/A activity by low-resolution BACS immunofluorescence represents the first multi-well cellular assay of BoNT/A activity to date, which is a significant advancement over the prior art that relied on Western blotting (19, 22). Thus, the ability to measure BoNT/A proteolytic activity in a high-throughput assay represents a breakthrough in antitoxin development, and will allow for the thorough evaluation of BoNT/A inhibitors in cell models of intoxication. Moreover, the higher sample throughput of the assay provides a practical means of measuring inhibitor potencies at multiple concentrations. This should facilitate the calculation of IC50 (half maximal inhibitory concentration) values in cell models. Additionally, the assay also possesses the potential to be used to 1) screen small-molecule compound libraries for novel BoNT/A antagonists and, 2) identify compounds that target other cellular pathways in addition to those that directly inhibit the toxin. Based on our results the most useful inhibitor screening strategy may involve linking our low- and high-resolution immunofluorescence approaches (FIGS. 12-15). In particular, primary screens could be conducted with the LR-BACS immunofluorescence assay (FIGS. 12, 14), allowing compounds to be rapidly evaluated. This step could be followed by secondary screens employing high-resolution BACS immunofluorescence (FIG. 13) as a component of high-content imaging to rescreen compound "hits," thereby enabling additional parameters such as compound toxicity and potential mode of action to be assessed.

Having now generally described this invention, the same will be better understood by reference to specific examples, which are included herein for purposes of illustration, and are not intended to be limiting unless otherwise specified.

Example 1

Method of Specific Antibody Production

Buffers

The following buffers may be used by way of non-limiting example: phosphate-buffered saline (PBS) Ph 7.4, or supplemented with 0.05% tween-20 (PBST), and cell lysis buffer consisting of 20 Mm Tris-HCl (Ph 7.5), 150 Mm NaCl, 1 Mm EDTA, 1 Mm EGTA, 1% Triton X-100, and Complete protease inhibitor cocktail (Roche, Manheim, Germany).

Generation of BoNT/A Cleavage Sensitive (BACS) Antibodies

BACS antibodies were generated by synthesizing three antigenic peptides that correspond to the BoNT/A cleavage site in SNAP-25 (FIG. 2), injecting these peptides into rabbits, and purifying antibodies from vaccinated rabbit sera. Each peptide was conjugated to keyhole limpet hemocyanin and injected into three rabbits. The peptides corresponded to SNAP-25 (accession no. P60880) residues:

1) 191-206 RIDEANQRATKMLGSG (SEQ ID NO. 1), which produced antibodies designated as F2068, F2069 and F2070;

2) 193-206 DEANQRATKMLGSG (SEQ ID NO. 2), which resulted in antibodies designated as F2692, F2693 and F2695; and, 3) 191-204 RIDEANQRATKMLG (SEQ ID NO. 3), which generated antibodies designated as F2689, F2690, and F2691.

After initial injections, the rabbits were periodically boosted with antigen, and serum was collected throughout the injection schedule. Seventy-two days after the initial injection, animals were bled for the final time, and serum was pooled for antibody purification. Affinity chromatography purification of the antibodies was performed on 50 ml cyanogen bromide-activated sepharose columns conjugated with the same peptides used for vaccinations. The method involved applying serum to the columns, washing with low salt buffer, and developing with a step Ph gradient (5, 4, 3, and 2) to elute the tightly associated antibodies. Peak fractions eluting during the Ph gradient were pooled and dialyzed against PBS.

Example 2

Western Blot In Vivo Assay for Botulinum Type A Toxin (BoNT/A)

Cell Model of BoNT/A Intoxication

Embryonic chicken spinal motor neurons were cultured by the method described previously by Kuhn (20) and used as a cellular model for BoNT/A intoxication as described by Stahl et al. (19). In brief, motor neurons were dissociated from dissected embryonic chicken spinal cords, plated, and intoxicated by diluting BoNT/A (MetaBiologics Inc., Madison, Wis.) into the cell culture medium. The cells were incubated with toxin at 37° C. for 3 to 5 hr and processed by the analytical methods described below.

Western Blot Analysis

Neurons treated with different concentrations of BoNT/A were washed and resuspended in PBS, transferred to microfuge tubes, pelleted by a brief, low speed centrifugation, and lysed by suspension in cell lysis buffer. Protein concentration within cleared whole cell lysate samples was determined by the Bradford protein assay (BioRad, Hercules, Calif.) with bovine serum albumin as a standard. Immunoblot analysis was conducted by resolving cell lysates (20 μg of protein per sample) on 12% Tris-glycine acrylamide gels (Invitrogen, Carlsbad, Calif.), transferring proteins to PVDF membranes, and probing membranes with primary antibody/secondary antibody pairs (FIG. 3). The SMI-81 antibody (Abcam Inc., Cambridge, Mass.) detects full-length SNAP-25 and the large N-terminal fragment produced by BoNT/A cleavage. The percentage of full-length SNAP-25 present in individual samples was calculated by measuring integrated band volumes and dividing the volume of the full-length band by the total SNAP-25 volume (full-length/(full-length+N-terminal fragment)). Custom made BACS antibodies, which only recognize full-length SNAP-25 protein, were analyzed by immunoblotting where indicated. For Western blot experiments that employed horseradish peroxidase (HRP)-conjugated secondary antibodies, images were visualized and digitized with the Biorad VersaDoc 4000 imaging system using Quantity One v4.6.2 analysis software (BioRad, Hercules, Calif.).

Example 3

Direct ELISA In Vivo Assay for Botulinum Type A Toxin (BoNT/A)

Direct ELISA

A microtiter plate (Immulon 2HB ELISA strips, Santa Cruz biotechnology, Santa Cruz, Calif.) was coated with either neuronal whole cell lysate samples diluted to 12 µg/ml with PBS containing protease inhibitors (Complete, Roche, Mannheim, Germany), or a dilution series of recombinant SNAP-25 protein (GenWay Biotech, San Diego, Calif.). Samples were plated in duplicate (the format of the assay required a sample to be split into two wells to allow for measurement with both detection antibodies), and allowed to adsorb to wells during a 2-hr incubation at 37° C. After adsorption, detection antibodies (400 ng/well) were added to appropriate wells and samples were incubated at 25° C. for 1 hr with shaking. The set of detection antibodies consisted of an N-terminal-specific SNAP-25 antibody (66066, Santa Cruz biotechnology, Santa Cruz, Calif.) and a BACS antibody (F2691) (FIG. 5). To enable the quantitation of detection antibody binding, HRP-conjugated goat anti-rabbit (ICN/Cappel, Solon, Ohio) and HRP-conjugated sheep anti-mouse secondary antibodies (GE Healthcare, Buckinghamshire, England) were added to samples containing either the BACS antibody or the N-terminal SNAP-25 antibody, respectively (FIG. 5). Both secondary antibodies were added at a concentration of 1 µg/ml and were incubated with the samples for 1 hr at 37° C. Finally, 100 µl of a chromogenic substrate (3,3,5,5-tetramethyl benidine (Turbo TMB) Thermo Scientific, Rockford, Ill.) was added to each well. The reaction was allowed to proceed for 15 min and then stopped by adding 2N $H_2SO_4$. The absorbance in each sample was measured at 450 nm using a multi-well absorbance spectrophotometer (Tecan, San Jose, Calif.) (FIGS. 6,7). Between all conjugation and binding steps described above, plates were washed three times with PBS. All data points presented herein are averages of two independent measurements.

Example 4

Capture ELISA In Vivo Assay for Botulinum Type A Toxin (BoNT/A)

Capture ELISA

A goat anti-mouse IgG microtiter plate (Reacti-Bind, Thermo Scientific, Rockford, Ill.) was coated with 250 ng/well of an N-terminal SNAP-25 "capture" antibody (66066, Santa Cruz biotechnology, Santa Cruz, Calif.) according to the manufacturer's recommendations (FIG. 7). Neuronal whole cell lysate samples, diluted to 10 µg/ml in PBST supplemented with protease inhibitors (Complete, Roche, Mannheim, Germany), and a dilution series of recombinant SNAP-25 protein (GenWay Biotech, San Diego, Calif.) were allowed to bind the coated plate during a 1-hr incubation at 37° C. After the capture step, BoNT/A cleavage-sensitive "detection" antibody F2070 was added to the plate at a concentration of 400 ng/well, and samples were incubated at 37° C. for 1 hr. To measure the detection antibody, HRP-conjugated goat anti-rabbit secondary antibody (ICN/Cappel, Solon, Ohio) was added to each well at a concentration of 1 µg/ml, and the plate was then incubated for 37° C. for 1 hr (FIG. 8). Finally, 100 µl of Turbo TMB (Thermo Scientific, Rockford, Ill.) was added to each well. The reaction was allowed to proceed for 15 min and then terminated by adding 2N $H_2SO_4$. The absorbance in each sample was measured at 450 nm using a multi-well absorbance spectrophotometer (Tecan, San Jose, Calif.) (FIGS. 9,10). Between all conjugation and binding steps described above, plates were washed three times with PBST. All data points presented here are averages of two independent measurements.

Example 5

Low Resolution Fluorescence In Vivo Assay for Botulinum Type A Toxin (BoNT/A)

Low Resolution Fluorescence Imaging (in-Cell Western Blot) Analysis Using BACS Antibodies Chick spinal cord motor neurons were dissociated, cultured in poly lysine coated 96-well plates (Greiner, Kremsmuenster, Austria), treated with BoNT/A, and analyzed by low-resolution fluorescence imaging (in-cell Western blotting). Assays were conducted by fixing/permeabilizing cells after intoxication, staining the cells with SNAP-25 antibodies (BACS antibody F2070 and N-terminal specific antibody SMI-81 (Abcam Inc., Cambridge, Mass.)) and species-specific fluorescent secondary antibodies (Li-Cor, Lincoln, Nebr.). Wells were then analyzed using the Li-Cor Odyssey infrared imaging system (Li-Cor, Lincoln, Nebr.), which measures fluorescence emission in two channels (700 and 800 nm) (FIGS. 12, 14, 15). In all experiments reported herein, the ratio of fluorescence intensity at 700 and 800 nm was measured for each well. These channels correspond to a normalization signal (N-terminal specific antibody staining) and BACS antibody-associated fluorescence, respectively. Initial experiments measured changes in fluorescence as a function of BoNT/A concentration (0-20 Nm) and allowed antibody dilutions to be optimized. Follow-up experiments measured assay robustness across 96-well plates by treating 30 wells with 2 Nm BoNT/A and 30 wells with medium alone. In these experiments the quality of the assay was assessed by calculating the z-score for the method (FIG. 14). Finally, the ability of the assay to be used for BoNT/A inhibitor screening was investigated using a known BoNT/A antagonist. Neurons were treated with either BoNT/A neutralizing antibody 4A2-421, or a control antibody previously shown to be effective against staphylococcal enterotoxin B (SEB) (Toxin Technology, Sarasota, Fla.) at concentrations of 1 µg/ml at the time of intoxication with 2 Nm BoNT/A (FIG. 15). Samples were then analyzed with optimized imaging parameters. In this experiment all samples were analyzed in replicates of six.

Example 6

High-Resolution Fluorescence In Vivo Assay for Botulinum Type A Toxin (BoNT/A)

High-Resolution Fluorescence Imaging Using BACS Antibodies

Chick spinal neurons were plated onto poly-L-lysine/laminin-coated Lab-Tek 8-well chamber slides (Nalge-Nunc, Naperville, Ill.) and exposed to an exchange of medium or to medium with 5 Nm BoNT A for 3 hr. After three rinses in medium, the cells were fixed in 3.7% formaldehyde for 30 min and permeabilized with 0.2% Triton-X-100 for 15 min. Cells were blocked in 2% bovine serum albumin then stained with SMI-81 and BACS antibody F2070 followed by Alexa 488 conjugated anti-mouse and Alexa 568 anti-rabbit secondary antibodies. Images were acquired on a BioRad (Hercules, Calif.) 2000 MP confocal/multiphoton system connected to a Nikon (Melville, N.Y.) TE300 inverted microscope. Images were thresholded identically and integrated fluorescence intensities were measured with MetaMorph software (Molecular Devices, Downingtown, Pa.) to obtain fluorescence ratios (FIG. 13).

Example 7

Data Modeling of In Vivo Assay for Botulinum Type A Toxin (BoNT/A)

ELISA experiments measuring BACS antibody binding as a function of recombinant SNAP-25 concentration were analyzed by nonlinear regression analysis using the program GraphPad Prism, version 5.01 (La Jolla, Calif.). The measured isotherms were fit to a one-site binding model (Hill equation), which allowed Hill coefficients (h) and dissociation constants (Kd) to be determined (equation 1).

$$y = B\max[x^h]/(K_d^h + [x^h]) \quad (1)$$

In this equation y is the absorbance at 450 nm measured by ELISA, Bmax is the maximum value of y measured at saturating substrate concentration, and [x] is the concentration of SNAP-25. All binding isotherms fit well to this model with $R^2$ values greater than 0.99, and yielded hill coefficients that approached unity. Dissociation constants determined for the four BACS antibodies are provided in the Results section.

Other embodiments and uses of the invention will be apparent to those skilled in the art from consideration of the specification and practice of the invention disclosed herein. All references cited herein, including all publications, U.S. and foreign patents and patent applications are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

All anti-peptide antibodies may be polyclonal in origin although it is just as feasible to perform the assay with monoclonal antibodies raised against the appropriate peptide.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

REFERENCES CITED

All references are incorporated herein in their entirety.
1. Alonso, P. L., et al., Duration of protection with RTS,S/AS02A malaria vaccine in prevention of Plasmodium falciparum disease in Mozambican children: single-blind extended follow-up of a randomized controlled trial. Lancet, 2005. 366 (9502): p. 2012-8.
1. Ting P T, Freiman A: The story of Clostridium botulinum: from food poisoning to Botox. Clin Med 2004; 4:258-261.
2. Turton K, Chaddock J A, Acharya K R: Botulinum and tetanus neurotoxins: structure, function and therapeutic utility. Trends Biochem Sci 2002; 27:552-558.
3. Kreyden O P, Geiges M L, Boni R, Burg G G: Botulinum toxin: from poison to drug. An historical review. Hautarzt 2000; 51:733-737.
4. Botulism associated with commercially canned chili sauce—Texas and Indiana. Morb Mortal Wkly Rep 2007; 56:767-769.
5. Domingo R M, Haller J S, Gruenthal M: Infant botulism: two recent cases and literature review. J Child Neurol 2008; 23:1336-1346.
6. Fox C K, Keet C A, Strober J B: Recent advances in infant botulism. Pediatr Neurol 2005; 32:149-154.
7. Godeiro-Junior C, Felicio A C, Aguiar P C, Borges V, Silva S M, Ferraz H B: Neuroleptic-induced tardive cervical dystonia: clinical series of 20 patients. Can J Neurol Sci 2009; 36:222-226.
8. Madalinski M, Kalinowski L: Novel options for the pharmacological treatment of chronic anal fissure—role of botulin toxin. Curr Clin Pharmacol 2009; 4:47-52.
9. Sun-Edelstein C, Mauskop A: Complementary and alternative approaches to the treatment of tension-type headache. Curr Pain Headache Rep 2008; 12:447-450.
10. Young W B, Marmura M, Ashkenazi A, Evans R W: Expert opinion: Greater occipital nerve and other anesthetic injections for primary headache disorders. Headache 2008; 48:1122-1125.
11. Dembek Z F, Kortepeter M G, Pavlin J A: Discernment between deliberate and natural infectious disease outbreaks. Epidemiol Infect 2007; 135:353-371.
12. Burnett J C, Henchal E A, Schmaljohn A L, Bavari S: The evolving field of biodefence: therapeutic developments and diagnostics. Nat Rev Drug Discovery 2005; 4:281-297.
13. Tseng-Ong L, Mitchell W G: Infant botulism: 20 years' experience at a single institution. J Child Neurol 2007; 22:1333-1337.
14. Lacy D B, Tepp W, Cohen A C, DasGupta B R, Stevens R C: Crystal structure of botulinum neurotoxin type A and implications for toxicity. Nat Struct Biol 1998; 5:898-902.
15. Dressler D, Adib Saberi F: Botulinum toxin: mechanisms of action. Eur Neurol 2005; 53:3-9.
16. Brunger A T, Breidenbach M A, Jin R, Fischer A, Santos J S, Montal M: Botulinum neurotoxin heavy chain belt as an intramolecular chaperone for the light chain. PLoS Pathog 2007; 3:1191-1194.
17. Blasi J, Chapman E R, Link E, Binz T, Yamasaki S, De Camilli P, et al: Botulinum neurotoxin A selectively cleaves the synaptic protein SNAP-25. Nature 1993; 365:160-163.
18. Schiavo G, Rossetto O, Catsicas S, Polverino de Laureto P, DasGupta B. et al: Identification of the nerve terminal targets of botulinum neurotoxin serotypes A, D, and E. J Biol Chem 1993; 268:23784-23787.
19. Stahl A M, Ruthel G, Torres-Melendez E, Kenny T A, Panchal R G, Bavari S: Primary cultures of embryonic chicken neurons for sensitive cell-based assay of botulinum neurotoxin: implications for therapeutic discovery. J Biomol Screen 2007; 12:370-377.
20. Kuhn T B: Growing and working with spinal motor neurons. Methods Cell Biol 2003; 71:67-87.
21. Pless D D, Tones E R, Reinke E K, Bavari S: High-affinity, protective antibodies to the binding domain of botulinum neurotoxin type A. Infect Immun 2001; 69:570-574.
22. Eubanks L M, Hixon M S, Jin W, Hong S, Clancy C M, Tepp W H, et al: An in vitro and in vivo disconnect uncovered through high-throughput identification of botulinum neurotoxin A antagonists. Proc Natl Acad Sci USA 2007; 104:2602-2607.

23. Archer, III, B. T, Ozcelik, T, Jahn, R., Francke, U. and Sudhof, T. C., “Structures and chromosomal localizations of two human gene encoding synaptobrevins 1 and 2,”. Biol. Chem. 265: 17267-17273 (1990).

24. Oyler, G. A., Higgins, G. A., Hart, R A., Battenberg, E., Billingsley, M., Bloom, F. E. and Wilson, M. C., “The identification of novel synaptosomal-associated protein SNAP-25, differentially expressed in neuronal subpopulations,” J. Cell Biology 109: 3039-3052 (1989).

25. Schiavo, G., Santucci, A., DasGupta, B. R, Mehta, P. P., Jontes, J., Benfenati, F., Wilson, M. C., and Montecucco, C., “Botulinum neurotoxins serotypes A and E cleave SNAP-25 at distinct COOH-terminal peptide bonds,” FEES Lett. 335: 50 99-103 (1993).

26. Bennett, M. K., Calakos, N., and Scheller, R. H., “Syntaxin: a synaptic protein implicated in docking of synaptic vesicles at presynaptic active zones,” Science 257: 255-259 55 (1992).

What is claimed is:

1. A proteolytic toxin assay comprising the steps of:
   (a) combining a test compound with a substrate and antibody, either sequentially or simultaneously, wherein the substrate has a cleavage site for a toxin and when cleaved by the toxin forms a product, wherein the antibody binds to the substrate but not to the product, wherein the substrate is within a cell; and,
   (b) detecting the presence of antibody bound to the substrate;
wherein said antibody binds selectively to a peptide having a sequence selected from the group consisting of:

```
                                        (SEQ ID NO: 1)
RIDEANQRATKMLGSG;

(SEQ ID NO: 2)
DEANQRATKMLGSG;
and, (SEQ ID NO: 3)
RIDEANQRATKMLG.
```

2. The assay of claim 1, wherein the substrate is an intact peptide or fragment thereof selected from the group consisting of SNAP-25, a SNAP-25 analog; and, a SNAP-25 isoform.

3. The assay of claim 1, wherein the antibody is detected using a nitrocellulose membrane.

4. The assay of claim 1, wherein the antibody is detected using a solid-phase component selected from the group consisting of diazocellulose, glass, polystyrene, polyvinylchloride, polypropylene, polyethylene, dextran, nylon, starch or affinity support gels.

5. The assay of claim 1, wherein the antibody is detected using a immunohistochemical label selected from a group consisting of a reporter enzyme, a radioisotope, a fluorescent compound, a chemiluminescent compound; and, a bioluminescent compound.

6. The assay of claim 1, wherein the antibody is detected using a secondary antibody.

7. The assay of claim 1, wherein the antibody is detected using high-resolution immunofluorescence imaging.

8. The assay of claim 1, wherein the antibody is detected using low-resolution immunofluorescence imaging.

9. The assay of claim 1, wherein the antibody is detected by at least one primary screen comprising of a low-resolution BAGS immunofluorescence assay, followed by at least one secondary screen comprising of a high-resolution BAGS immunofluorescence assay.

10. A proteolytic toxin assay comprising the steps of:
    (a) combining a test compound with a substrate and antibody, either sequentially or simultaneously, wherein the substrate has a cleavage site for a toxin and when cleaved by the toxin forms a product, wherein the antibody binds to the substrate but not to the product, wherein the substrate is within a cell;
    (b) detecting the presence of antibody bound to the substrate; wherein said antibody binds selectively to a peptide having a sequence selected from the group consisting of:

```
                                        (SEQ ID NO: 1)
RIDEANQRATKMLGSG;

(SEQ ID NO: 2)
DEANQRATKMLGSG;
and, (SEQ ID NO: 3)
RIDEANQRATKMLG
and,
```

(c) using a normalized response to detect a decreased antibody signal.

11. The assay of claim 10, wherein the normalized response is calculated as a ratio between levels of full-length substrate and total substrate.

12. The assay of claim 1, wherein a normalized response is used to detect a decreased antibody signal.

13. The assay of claim 12, wherein the normalized response is calculated as a ratio between levels of full-length substrate and total substrate.

14. The assay of claim 1, wherein the substrate is an intact peptide or fragment thereof selected from the group consisting of SNAP-25, a SNAP-25 analog, a SNAP-25 isoform; wherein the said antibody binds selectively to a peptide having a sequence selected from the group consisting of:

```
                                        (SEQ ID NO: 1)
RIDEANQRATKMLGSG;

(SEQ ID NO: 2)
DEANQRATKMLGSG;
and, (SEQ ID NO: 3)
RIDEANQRATKMLG;
``` and further wherein the antibody is detected using immunofluorescence imaging.

\* \* \* \* \*

SEQUENCE LISTING

```
<160> NUMBER OF SEQ ID NOS: 4

<210> SEQ ID NO 1
<211> LENGTH: 16
<212> TYPE: PRT
<213> ORGANISM: Homo sapiens

<400> SEQUENCE: 1

Arg Ile Asp Glu Ala Asn Gln Arg Ala Thr Lys Met Leu Gly Ser Gly
1               5                   10                  15

<210> SEQ ID NO 2
<211> LENGTH: 14
<212> TYPE: PRT
<213> ORGANISM: Homo sapiens

<400> SEQUENCE: 2

Asp Glu Ala Asn Gln Arg Ala Thr Lys Met Leu Gly Ser Gly
1               5                   10

<210> SEQ ID NO 3
<211> LENGTH: 14
<212> TYPE: PRT
<213> ORGANISM: Homo sapiens

<400> SEQUENCE: 3

Arg Ile Asp Glu Ala Asn Gln Arg Ala Thr Lys Met Leu Gly
1               5                   10

<210> SEQ ID NO 4
<211> LENGTH: 205
<212> TYPE: PRT
<213> ORGANISM: Homo sapiens

<400> SEQUENCE: 4

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn Ile Gln Asp Met Lys Glu Ala Glu Lys Asn Leu Lys Asp Leu Gly
65                  70                  75                  80

Lys Cys Cys Gly Leu Phe Ile Cys Pro Cys Asn Lys Leu Lys Ser Ser
                85                  90                  95

Asp Ala Tyr Lys Lys Ala Trp Gly Asn Asn Gln Asp Gly Val Val Ala
            100                 105                 110

Ser Gln Pro Ala Arg Val Val Asp Glu Arg Glu Gln Met Ala Ile Ser
```

```
            115                 120                 125
Gly Gly Phe Ile Arg Arg Val Thr Asn Ala Asp Ala Arg Glu Asn Glu
        130                 135                 140

Met Asp Glu Arg Ile Glu Gln Val Ser Gln Ile Ile Gly Asn Leu Arg
145                 150                 155                 160

His Met Ala Leu Asp Met Gly Asn Glu Ile Asp Thr Gln Asn Arg Gln
                165                 170                 175

Ile Asp Arg Ile Met Glu Lys Ala Asp Ser Asn Lys Thr Arg Ile Asp
            180                 185                 190

Glu Ala Asn Gln Arg Ala Thr Lys Met Leu Gly Ser Gly
        195                 200                 205
```